United States Patent [19]

Miyazawa et al.

[11] Patent Number: 5,248,610
[45] Date of Patent: Sep. 28, 1993

[54] PROCESS FOR PRODUCING OPTICALLY ACTIVE α-HYDROXYESTERS USING LIPASE PS

[75] Inventors: Kazutoshi Miyazawa; Naoyuki Yoshida, both of Ichihara, Japan

[73] Assignee: Chisso Corporation, Osaka, Japan

[21] Appl. No.: 708,868

[22] Filed: May 31, 1991

[30] Foreign Application Priority Data

May 31, 1990 [JP] Japan .................................. 2-139869

[51] Int. Cl.$^5$ ............................................... C12P 7/22
[52] U.S. Cl. .................................... 435/280; 435/876
[58] Field of Search .............................. 435/280, 876

[56] References Cited

FOREIGN PATENT DOCUMENTS 1247100 3/1988 Japan .

OTHER PUBLICATIONS

Lazar et al., in World Conference on Emerging Technologies in the Fats and Oils Industry, ed. Baldwin, pp. 346–354 (1986).
Fitzpatrick, J. Am. Chem. Soc. 113:3166–71 (1991).
Hsu et al, Tetrahedron Lett. 31:6403–6406 (1990).
Wang et al, J. Am. Chem. Soc. 110:7200–7205 (1988).
Bianchi D, J. Org. Chem 53:5531–34 (1988).
Klibanov A, Acc. Chem. Res. 23:114–120 (1990).
Okumura S, BBA 575:156–165 (1979).
Hills M, BBA 1042:237–240 (1990).

Primary Examiner—Douglas W. Robinson
Assistant Examiner—S. Saucier
Attorney, Agent, or Firm—Wenderoth, Lind & Ponack

[57] ABSTRACT

The invention provides a process for producing an optically active α-hydroxyester by a biochemical method, and the process comprises reacting an ester with a racemic compound in the presence of a lipase to obtain the following compound which are useful for starting materials for physiological active materials, functional materials and the like.

$$A-\overset{\overset{\displaystyle OH}{|}}{C^*}HCOOR \qquad (I)$$

wherein R is alkyl of 1–5 carbon atoms, A is alkyl of 1–20 carbon atoms, perfluorophenyl, 2-phenylethyl or a specific phenyl group.

2 Claims, 3 Drawing Sheets

PROCESS FOR PRODUCING OPTICALLY ACTIVE α-HYDROXYESTERS USING LIPASE PS

BACKGROUND OF THE INVENTION

1. Field of the Invention

The present invention relates to a process for producing optically active compounds which are useful as starting materials for physiologically active materials, functional materials and the like, especially to a process for producing optically active α-hydroxyesters.

2. Description of the Prior Art

Optically active compounds are useful chemical compounds as starting materials or intermediates for physiologically active materials of medical supplies, agricultural chemicals and the like. However, the compounds have optical isomers and in practical use it is necessary to use only one of these antipodes. Further, when racemates or compounds having low optical purity are used, the obtained compounds apparently do not develop enough physiological activity or functionability.

The optically active compounds obtained by the process of the present invention, namely, optically active α-hydroxyesters are very useful compounds.

From the optically active α-hydroxyesters, optically active haloesters (B. J. Lee, et al., Tetrahedron, 23, 359(1967), optically active glycols (V. Prelog, et al., Helv. Chim, Acta. 37, 234(1954)), optically active epoxides (K. Mori, et al., Tetrahedron, 35, 933(1979)) and the like which are useful for optically active compounds can be derived. Especially, the optically active epoxides are useful for starting materials for synthesizing ferroelectric liquid crystal compounds which are particularly useful. (Nohira et al. The 12th Forum of liquid crystals, Preprints, 2F11(1986), Nohira et al. The 12th Forum of liquid crystals, Preprints, 1Z02(1987)).

Additionally, the compounds represented by the formula (1) below wherein A is phenyl or a substituted phenyl, which are easily derived by hydrolysis to optically active α-hydroxyphenylacetic acid or optically active α-hydroxysubstituted-phenylacetic acid, are useful for optical resolving agents. For example, the compounds are usable for optical resolving agents of medical or agricultural supplies such as 2-amino-1-butanol which is a starting material of antituberculous ethambutol, diltiazem hydrochloride which a coronary vasodilator and tetramizol effective as an anthelmintic (Japanese Patent Publication No. 61-52812, and Japanese Patent Unexamined Publication Nos. 58-32872 and 62-192388).

Further, the compounds are useful for optically resolving agents of α-amino acids such as alanine, phenyl alanine, methionine, cysteine and the like (Japanese Patent Unexamined Publication Nos. 55-57545 and 60-32752, Japanese Patent Publication No. 58-1105, and Japanese Patent Unexamined Publication Nos. 59-181244, 57-193448 and 59-51239).

Compounds represented by the formula (1) below wherein A is 2-phenylethyl, which are easily derived to 2-amino-4-phenylbutanoates, are starting materials for synthesizing enalapril which is an ACE inhibitor (angiotensinconverting enzyme inhibitor) and the like.

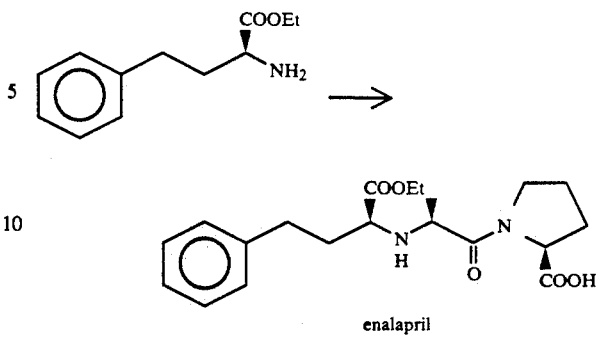

enalapril (H. Urbach and R. Henning, Tetrahedron Lett., 25, 1143(1984)).

The compounds represented by the formula (I) are useful as described above. However, no effective process for producing optically active compounds is known.

As an example, there is a process of asymmetric reduction of α-ketoesters with a microorganism or baker's yeast. (K. Nakamura et al., J. Org. Chem., 53, 2589(1988), K. Nakamura et al., Tetrahedron Letters., 29, 2453(1988), Japanese Patent Unexamined Publication No. 62-61587).

However, since the reaction efficiency of these methods are bad and the objective compounds having desired optical purity are not always obtained, these methods are not industrially useful methods.

In chemical reduction of α-ketoesters, a method wherein optically active α-hydroxyesters are obtained by using arylglyoxylic acid is reported. However, since the asymmetric yield is very bad (2.4-9.7%ee), it cannot be said that the method is practical (I. Takahashi et al., Chem. Pharm. Bull., 33 3571(1985)).

A method wherein optically active α-hydroxyesters are obtained by asymmetric reduction with an organic boron compound in a high yield is also reported. However, the organic boron compound is very expensive and a strict reaction condition of a temperature of −78° C. is required. Accordingly, it is difficult to say that the method is industrially useful (H. C. Brown et al., J. Org. Chem., 53, 1231(1988)).

On the other hand, optically active α-hydroxyesters can be obtained by esterification of optically active carboxylic acids. However, as the α-hydroxy carboxylic acids obtainable commercially, only lactic acid and mandelic acid are known (K. Motosugi et al., Biotechnol. and Bioeng., 26, 805(1984), Keiichiro Hiyama, Separation Technics, 16 360(1986)). To obtain the other α-hydroxy carboxylic acids, a method for recrystallizing by using optically active natural alkaloids such as brucine and the like should be used. Namely, salts which are obtained from racemic α-hydroxy carboxylic acids and natural alkaloids such as brucine and the like are recrystallized. The crystals obtained and salts which are recovered from mother liquor are hydrolyzed in water, respectively, to obtain optically active α-hydroxy carboxylic acids. However, the method has problems that the recrystallization should be made several times or dozens of times to obtain optically pure α-hydroxy carboxylic acids and the alkaloids should be recovered. Further, the method for recovering the alkaloids is troublesome. Accordingly, the method is not an advantageous method industrially and economically.

In spite of the usefulness, a better process for producing the optically active α-hydroxyesters is not known, so that an efficient, economical and technical process is long-desired.

As mentioned above, the efficiency of the conventional methods is very bad, and products having enough asymmetric yield are seldom obtained.

SUMMARY OF THE INVENTION

The present invention aims to solve the problems of the conventional methods and to provide a process for producing optically active α-hydroxyesters which is a new and efficient method.

The present invention provides a process for producing an optically active α-hydroxyester, characterized in that it comprises reacting an ester with a racemic compound of the formula:

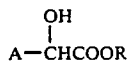
          (I)

wherein
R is alkyl of 1-5 carbon atoms,
A is a member selected from the group consisting of alkyl of 1-20 carbon atoms, perfluorophenyl, 2-phenylethyl or a group of the formula:

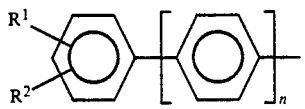

wherein n is 0 or 1, $R^1$ and $R^2$ are halogen, hydroxyl, alkyl of 1-20 carbon atoms, alkoxy, amino or hydrogen, under substantially anhydrous conditions and in the presence of an enzyme to effect a transesterification reaction and obtaining an R- or S-alcohol and the corresponding S- or R-ester of the alcohol represented by the formula:

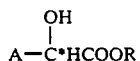
          (II)

wherein R and A are the same as described above.

In the process of the present invention, the reaction is conducted under substantially anhydrous conditions.

This process does not require the use of a small amount of lower alcohol instead of water, so that the esters for transesterification or the esters obtained are not hydrolyzed. No side reaction occurs with a formation of undesired esters. The enzyme is easily separated after the reaction and re-used. Furthermore, since the reaction of the present invention is conducted under substantially anhydrous conditions, the reaction zone can be kept free from contamination of undesired microorganisms. There is no necessity for preparing a special equipment, antiseptics, sterilization treatment, etc.. It is possible to conduct the reaction in an open system. Further, the reaction may be conducted in the same or high substrate concentration in comparison with common organic synthetic reactions.

It is also sufficient to use esters for transesterification which are easily commercially available. Ethyl acetate, ethyl propionate, ethyl butyrate, ethyl stearate, trichloro-ethyl laurate, butyl laurate, ethylene glycol diacetate, triacetin, tripropionin, tributyrin, tricaproin, tristearin, trilaurin, trimyristin, triolein, etc. are usable.

Preferably, fatty acid vinyl esters such as vinyl acetate, vinyl caproate, vinyl laurate, etc. can be exemplified as the esters.

As the enzyme which is used in the present invention, hydroxylase is used, and a lipase, lipoprotein lipase, esterase, or the like is preferable. The enzyme has the ability to catalyse a transesterification reaction preferentially between the R- or S- compound and the ester when the enzyme is used with the (R,S)-compound, and the enzyme can be used regardless its class. The following table shows commercially available enzymes that can be used in the present reaction.

TABLE

| Trade name | Origin | Seller or Maker |
|---|---|---|
| Lipase AP | *Aspergillus niger* | Amano Pharmaceutical Co., Ltd |
| Lipase M | *Mucor javanicus* | Amano Pharmaceutical Co., Ltd |
| Lipase P | *Pseudomonas fluorescens* | Amano Pharmaceutical Co., Ltd |
| Lipase PS | *Pseudomonas fluorescens* | Amano Pharmaceutical Co., Ltd |
| Lipase CES | *Pseudomonas sp* | Amano Pharmaceutical Co., Ltd |
| Lipase CE | *Humicola lanuginosa* | Amano Pharmaceutical Co., Ltd |
| Lipase AP | *Rhizopus javanicus* | Amano Pharmaceutical Co., Ltd |
| Lipase II | *Porcine Pancreas* | Sigma Chemical Co. |
| Lipase VIII | *Geotrichum Candidum* | Sigma Chemical Co. |
| Lipase X | *Rhizopus delamar* | Sigma Chemical Co. |
| Lipase | *Chromobacterium Viscosum* | Toyo Jozo Co., Ltd. |
| Palatase A | *Aspergillus niger* | Novo Industi A/S |
| Lipase | *Rhizopus niveus* | Nagase Biochemicals, Ltd. |
| Lipase B | *Pseudomonas fragi* | Sapporo Beer Co. |

In addition to these enzymes, the enzymes produced from microorganisms which produce the enzymes having the above ability can be used regardless of their species and genus. As such microorganisms, the genera Arthrobacter, Acromobacter, Alcaligenes, Aspergillus, Chromobacterium, Candida, Mucor, Pseudomonas, Rhizopus, etc. can be exemplified.

The process for producing the optically active compound of the present invention is described in more detail below.

In the present invention, the racemic compounds of the raw materials represented by the above formula (I) can be prepared by common organic chemical techniques. For example, the compounds can be effectively prepared by the following process:

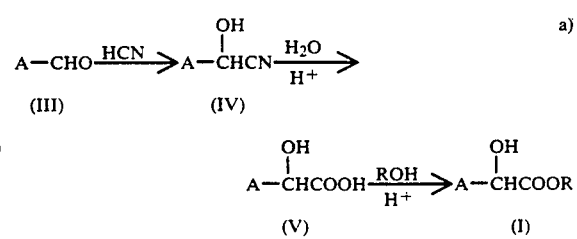

wherein A and R are the same as the formula (I) described above.

Namely, an aldehyde (III) is reacted with hydrogen cyanide, and the cyanohydrin (IV) obtained is hydrolyzed and esterifed to prepare the racemic compound. (e.g. B. B. Corson, et al., Org. Synth., Coll. Vol. 1, 336(1941)).

$$A-\underset{\text{(VI)}}{\overset{O}{\overset{\|}{C}}CH_3} \xrightarrow{Cl_2} A-\underset{\text{(VII)}}{\overset{O}{\overset{\|}{C}}CHCl_2} \xrightarrow[\text{base}]{H_2O} \quad b)$$

$$A-\underset{\text{(V)}}{\overset{OH}{\overset{|}{C}}HCOOH} \xrightarrow[H^+]{ROH} A-\underset{\text{(I)}}{\overset{OH}{\overset{|}{C}}HCOOR}$$

wherein A and R are the same as the formula (I) described above.

Namely, an acetylated compound (VI) is chlorinated, the dichloride (VII) obtained is hydrolyzed and esterified to prepare the racemic compound. (e.g. J. G. Aston, Org. Synth., Coll. 3, 538(1955)).

$$A-CHO \xrightarrow[\text{NaCN}]{\text{NaHSO}_3} A-\underset{\text{(V)}}{\overset{OH}{\overset{|}{C}}HCOOH} \xrightarrow[H^+]{ROH} A-\underset{\text{(I)}}{\overset{OH}{\overset{|}{C}}HCOOR} \quad c)$$

wherein A and R are the same as the formula (I) described above.

Namely, an aldehyde (III) is reacted with sodium cyanide and sodium bisulfite, the compound obtained (V) is esterified and the desired racemic compound (I) can be obtained.

In the present invention, the reaction is conducted by contacting efficiently the racemic compound with an ester and an enzyme.

The racemic compound used in this process can be used without any particular treatment. When the racemic compound is soluble in the ester, the reaction can be conducted without solvent. When the racemic compound is slightly soluble in the ester, an organic solvent such as heptane, toluene, ethyl acetate and the like may be added.

The reaction temperature is suitably 0° to 100° C., it is changeable by the class of the enzyme, and especially preferable is a temperature of 15° to 45° C.

The reaction time is changeable by the class of the substrate for periods of from 5 to 200 hours. The reaction time can be shortened by changing the reaction temperature, the enzyme class and the substrate concentration.

The racemic compound which is a substrate and the ester are suitably mixed in the ratio 1:0.4 to 1:2 by mole, preferably 1:0.5 to 1:1 by mole. Though, excess quantity of the ester may be used.

After the transesterification reaction as described above, the enzyme can be removed by conventional filter operation and used again, as it is. Otherwise, the reaction can be repeated by using the enzyme which is adsorbed and fixed on a hydrophobic resin and the like. The reactant which is the filtrate can be separated into an optically active alcohol and an optically active ester which is an ester of the enantiomer of the alcohol, respectively, for instance by distillation or column chromatography. The obtained optically active ester is hydrolyzed to derive the optically active alcohol which is an antipode of the said optically active alcohol.

The optically active alcohols have little different optical purities based on the difference of the structure, and the optical purities can be increased by retransesterification.

Compounds which can be efficiently resolved into the corresponding optically active compounds by the above process of the present invention are exemplified in the following.

2-hydroxypropionate (Example 3)
2-hydroxybutanoate (Example 4)
2-hydroxypentanoate
2-hydroxyhexanoate (Example 5)
2-hydroxyheptanoate
2-hydroxyoctanoate
2-hydroxynonanoate
2-hydroxydecanoate (Example 8)
2-hydroxyundecanoate
2-hydroxydodecanoate
2-hydroxytridecanoate
2-hydroxytetradecanoate
2-hydroxypentadecanoate
2-hydroxyhexadecanoate
2-hydroxyheptadecanoate
2-hydroxyoctadecanoate
2-hydroxynonadecanoate
α-hydroxyperfluorophenylacetate
α-hydroxyphenylacetate (Example 1)
α-hydroxy-4-hydroxyphenylacetate (Example 6)
α-hydroxy-4-fluorophenylacetate (Example 7)
α-hydroxy-4-bromophenylacetate (Example 2)
α-hydroxy-4-chlorphenylacetate
α-hydroxy-3,4-dihydroxyphenylacetate
2-hydroxy-2-biphenylylacetate
2-hydroxy-2-(4-hydroxy-4'-biphenylyl)acetate
2-hydroxy-2-(4-fluoro-4'-biphenylyl)acetate
2-hydroxy-2-(4-chlor-4'-biphenylyl)acetate
2-hydroxy-2-(3,4-didoroxy-4'-biphenylyl)acetate
2-hydroxy-2-(4-bromo-4'-biphenylyl)acetate
2-hydroxy-4-phenylbutanoate The merits of the present invention are as follows.

(1) Unnecessary hydrolysis of esters scarcely occurs because the transesterification reaction is conducted under substantially anhydrous conditions.

(2) The enzyme can be easily recovered and re-used.

(3) No special equipment and materials are used because the reaction can be performed under the conditions of relatively lower temperatures and an open system.

(4) Optically active substances having high purity are obtained by a one-step reaction.

(5) In spite of the biochemical reaction, the substrate concentration can be increased and large reaction vessels are unnecessary, because a buffer solution and the like are not required in the reaction.

DESCRIPTION OF THE PREFERRED EMBODIMENTS

The following examples illustrate the present invention more specifically. The optical purity of optically active compounds in the examples is determined by the following method: Comparison with specific rotation of a compound of which optical purity is known, Determination of $^1$H-NMR of esters (abbreviated as (+)-MTPA ester hereinafter) which are obtained by reaction with R-(+)-α-methoxy-α-(trifluoromethyl)phenylacetic acid, and HPLC analysis with an optical resolution column. The constitution of the compounds are determined by $^1$H-NMR, IR, GCMS, element analysis and the like.

Example 1

Optical resolution of (±)-methyl α-hydroxyphenylacetate (in the formula (I) R is methyl and A is phenyl)

Figure 1:
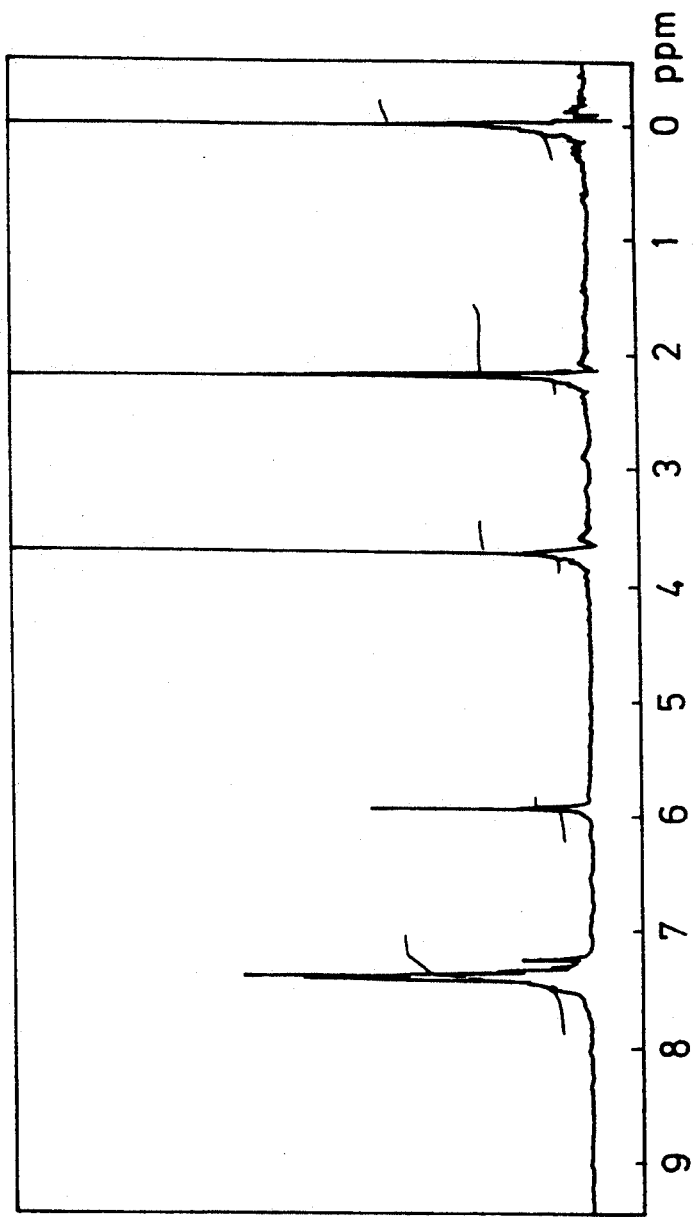
FIG. 1 is a chart of 90 MHz $^1$H-NMR spectrum of methyl S-α-acetoxyphenylacetate obtained in Example 1.

A mixture of 3.0 g of (±)-methyl α-hydroxyphenylacetate (18 mmol), 0.93 g (11 mmol) of vinyl acetate, 1.0 g of lipase PS (manufactured by Amano Pharmaceutical Co. Ltd.) and 20 ml of toluene was stirred for 72 hours at room temperature. After lipase PS was removed by suction filtration, the filtrate was chromatographed over silica gel (elution with toluene:ethyl acetate (3:1)), and the purified 1.41 g of methyl R-α-hydroxyphenylacetate (yield: 94%), $[\alpha]_D^{21}$ −125.4° (C 0.32, CH$_3$OH), and 1.66 g of methyl S-α-acetoxyphenylacetate (yield:89%) were obtained. The chart of $^1$H-NMR is shown in FIG. 1.

Figure 2:
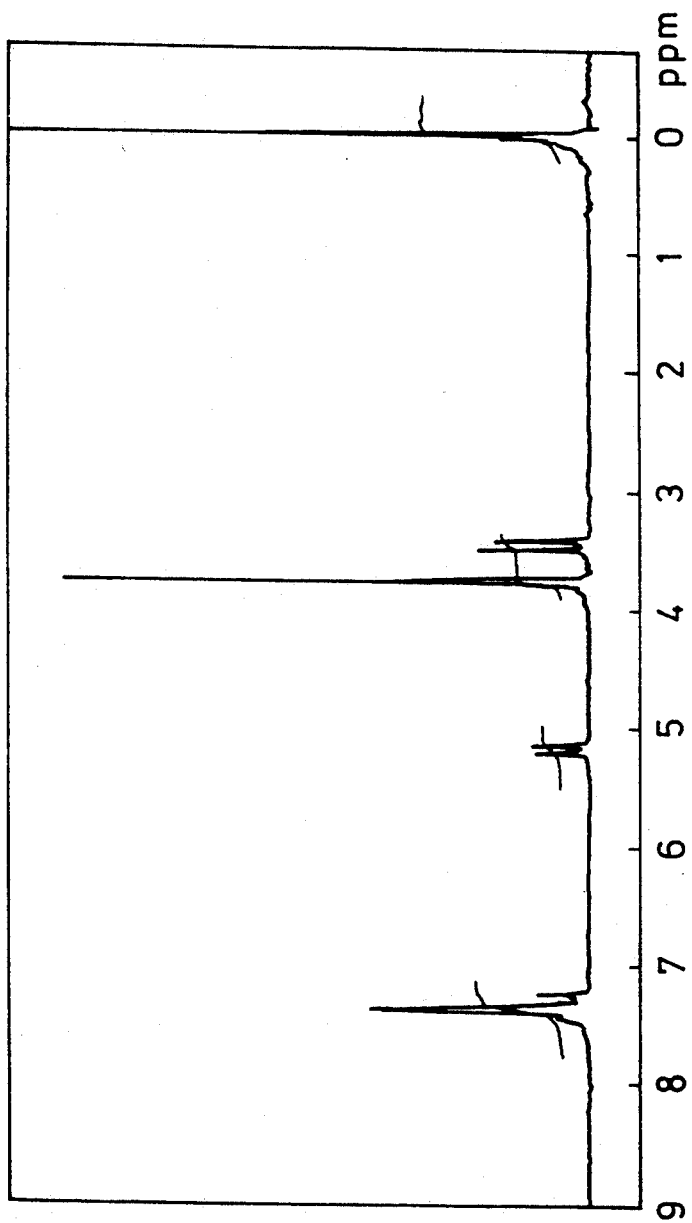
FIG. 2 is a chart of 90 MHz $^1$H-NMR spectrum of methyl S-α-hydroxyphenylacetate obtained in Example 1.

To 1.66 g of methyl S-α-acetoxyphenylacetate 5 ml of methanol and 3 drops of concentrated sulfuric acid are added. The mixture was stirred for 5 hours at a temperature of 40° C. to remove an acetyl group. 1.20 g of methyl S-α-hydroxyphenylacetate was obtained (yield: 90%). The chart of $^1$H-NMR is shown in FIG. 2.

$[\alpha]_D^{22}$ +134.2° (C 0.33, CH$_3$OH), 93.2%ee.

Example 2

Optical resolution of (±)-methyl 4-bromo-α-hydroxyphenylacetate (in the formula (I) R is methyl and A is p-bromophenyl)

(1) A mixture of 20 g (87 mmol) of (±)-4-bromo-α-hydroxyphenylacetic acid, 200 ml of methanol and 2 ml of concentrated sulfuric acid was stirred for 3 hours at room temperature. To the mixture 50 ml of water was added. After the solution was extracted with ethyl acetate, the organic extract was washed with a saturated aqueous solution of sodium bicarbonate and then with water, and it was dried on anhydrous magnesium sulfate. After removing the solvent, the residue was purified by chromatography (elution with toluene:ethyl acetate (2:1)), and 19.5 g of (±)-methyl 4-bromo-α-hydroxyphenylacetate was obtained (yield: 92%).

(2) A mixture of 4.4 g (18 mmol) of (±)-methyl 4-bromo-α-hydroxyphenylacetate obtained in (1), 0.93 g (11 mmol) of vinyl acetate, 1.0 g of lipase PS and 20 ml of toluene was stirred for 40 hours at room temperature. After lipase PS was removed by suction filtration, the filtrate was chromatographed over silica gel (elution with toluene:ethyl acetate (4:1)) to obtain 2.22 g of methyl R-4-bromo-α-hydroxyphenylacetate, $[\alpha]_D^{29}$ −67.5° (C 1.07, CHCl$_3$), 60%ee, and 1.61 g of methyl S-4-bromo-α-acetoxyphenylacetate (yield: 62.4%), $[\alpha]_D^{29}$ +106° (C 1.18, CHCl$_3$), 100%ee.

Figure 3:
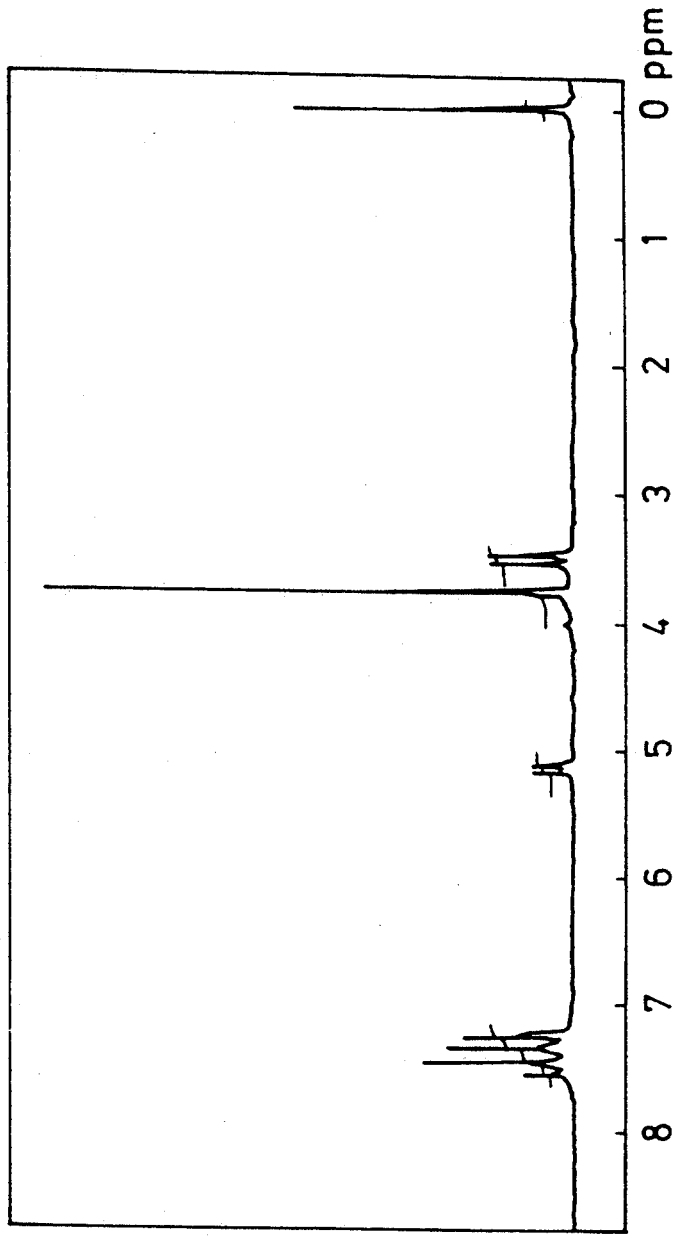
FIG. 3 is a chart of 90 MHz $^1$H-NMR spectrum of methyl R-4-bromo-α-hydroxyphenylacetate obtained in Example 2.

(3) A mixture of 2.22 g (9 mmol) of methyl R-4-bromo-α-hydroxyphenylacetate obtained in (2), 0.34 g (44 mmol) of vinyl acetate, 0.5 g of lipase PS and 10 ml of toluene was stirred for 30 hours at room temperature. After lipase PS was removed by suction filtration, the filtrate was chromatographed over silica gel (elution with toluene:ethyl acetate (4:1)) to obtain 1.67 g of methyl R-4-bromo-α-hydroxyphenylacetate, $[\alpha]_D^{30}$ −107° (C 1.10, CHCl$_3$), 98%ee, yield 75%, (the chart of $^1$H-NMR is shown in FIG. 3) and 0.60 g of methyl S-4-bromo-α-acetoxyphenylacetate, $[\alpha]_D^{28}$ +105° (C 0.98, CHCl$_3$).

Example 3

Optical resolution of (±)-butyl α-hydroxypropionate (in the formula (I) R is n-butyl and A is methyl)

(1) A mixture of 20.0 g (137 mmol) of (±)-butyl α-hydroxypropionate, 12.4 g (55 mmol) of vinyl laurate and 5.0 g of lipase PS (manufactured by Amano Pharmaceutical Co. Ltd.) was stirred for 24 hours at room temperature. After lipase PS was removed by suction filtration, the filtrate was purified by distillation, and 10.2 g of S-butyl α-hydroxypropionate, $[\alpha]_D^{25}$ −5.5° (neat), b.p. 41° C. (2.5 mmHg) and 14.2 g of R-butyl α-lauroyloxypropionate as the residue (yield:56%) 84%ee were obtained.

(2) A mixture of 10.2 g (70 mmol) of S-butyl α-hydroxypropionate obtained in (1), 6.3 g (28 mmol) of vinyl laurate and 2.5 g of lipase PS was stirred for 90 hours at room temperature. After lipase PS was removed by suction filtration, the filtrate was purified by distillation, and 7.1 g of S-butyl α-hydroxypropionate (yield: 70% from the racemic compound), $[\alpha]_D^{25}$ −11.4° (neat), 95%ee, b.p. 82° C. (18.5 mmHg), and as the residue, 2.9 g of R-butyl-α-lauroyl oxypropionate were obtained.

Example 4

Optical resolution of (±)-ethyl α-hydroxybutyrate (in the formula (I) R is ethyl and A is ethyl)

(1) A mixture of 5.25 g (39.7 mmol) of (±)-ethyl α-hydroxybutyrate, 3.6 g (15.9 mmol) of vinyl laurate and 0.5 g of lipase PS (manufactured by Amano Pharmaceutical Co. Ltd.) was stirred for 34 hours at room temperature. After lipase PS was removed by suction filtration, the filtrate was purified by distillation, and 3.5 g of S-ethyl α-hydroxybutyrate, $[\alpha]_D^{29}$ −1.95° (c 1.01, EtOH), b.p. 64° C. (19.5 mmHg) and 4.22 g of R-ethyl α-lauroylbutyrate as the residue were obtained.

A mixture of 4.22 g of R-ethyl α-lauroyloxybutyrate obtained above, 25 ml of ethanol and 0.1 ml of concentrated sulfuric acid was refluxed for 5 hours to remove an acyl group. 1.77 g of R-ethyl α-hydroxybutyrate was obtained (yield: 99%, 67% from the racemic compound), $[\alpha]_D^{28}$ +6.0° (C 1.2, EtOH), 77%ee, b.p. 56° C. (19 mmHg).

(2) A mixture of 3.5 g (26 mmol) of S-ethyl α-hydroxybutyrate obtained in (1), 2.26 g (10 mmol) of vinyl laurate and 0.5 g of lipase PS was stirred for 50 hours at room temperature. After lipase PS was removed by suction filtration, the filtrate was purified by distillation, and 2.1 g of S-ethyl α-hydroxybutyrate (yield: 60% from the racemic compound), $[\alpha]_D^{30}$ −7.33° (C 0.85, EtOH), 94%ee, b.p. 66° C. (20 mmHg), and 2.0 g of R-ethyl α-lauroyloxybutyrate as the residue were obtained.

Example 5

Optical resolution of (±)-ethyl α-hydroxyhexanoate (in the formula (I) R is n-ethyl and A is n-butyl)

(1) A mixture of 9.0 g (56 mmol) of (±)-ethyl α-hydroxyhexanoate, 5.1 g (22 mmol) of vinyl laurate and 2.0 g of lipase PS was stirred for 25 hours at room temperature. After lipase PS was removed by suction filtration, the filtrate was purified by distillation, and 5.7 g of R-ethyl α-hydroxyhexanoate, $[\alpha]_D^{29} +1.77°$ (neat), b.p. 80° C. (5 mmHg) and 7.0 g of S-ethyl α-lauroyloxyhexanoate was obtained.

A mixture of 7.0 g of S-ethyl α-lauroyloxyhexanoate obtained above, 40 ml of ethanol and 0.3 ml of concentrated sulfuric acid was refluxed for 6 hours to remove an acyl group. 2.85 g of S-ethyl α-hydroxyhexanoic acid was obtained, $[\alpha]_D^{30} -3.57°$ (neat), b.p. 84° C. (10 mmHg).

Example 6

Optical resolution of (±)-methyl 4-hydroxy-α-hydroxyphenylacetate (in the formula (I) R is methyl and A is p-hydroxyphenyl)

A mixture of 2.0 g (11 mmol) of (±)-methyl 4-hydroxy-α-hydroxyphenylacetate, 0.57 g (6.6 mmol) of vinyl acetate and 0.5 g of lipase PS was stirred for 120 hours at room temperature. After lipase PS was removed by suction filtration, the filtrate was chromatographed over silica gel (elution with toluene: ethyl acetate (1:1)), and the purified 1.23 g of R-methyl 4-hydroxy-α-hydroxyphenylacetate, $[\alpha]_D^{32} -67°$ (C 0.59, CHCl$_3$), 51%ee, and 1.14 g of S-methyl 4-hydroxy-α-acetoxyphenylacetate, $[\alpha]_D^{31} +112.5°$ (C 0.74, CHCl$_3$), 100%ee, yield: 92%, were obtained.

Example 7

Optical resolution of (±)-methyl 4-fluoro-α-hydroxyphenylacetate (in the formula (I) R is methyl and A is p-fluorophenyl)

A mixture of 3.0 g (16 mmol) of (±)-methyl 4-fluoro-α-hydroxyphenylacetate, 5.0 g of vinyl acetate and 1.0 g of lipase PS was stirred for 96 hours at room temperature. After lipase PS was removed by suction filtration, the filtrate was chromatographed over silica gel (elution with toluene:ethyl acetate (10:1)), and the purified 1.16 g of R-methyl 4-fluoro-α-hydroxyphenylacetate, $[\alpha]_D^{24} -99.5°$ (C 0.95, acetone), yield:77%, and 1.93 g of S-methyl 4-fluoro-α-acetoxyphenylacetate, $[\alpha]_D^{24} +101.6°$ (C 1.09, acetone), yield:100%, were obtained.

Example 8

Optical resolution of (±)-methyl 2-hydroxydecanoate (in the formula (I) R is methyl and A is n-octyl)

(1) A mixture of 241.5 g (1.18 mol) of (±)-methyl 2-hydroxydecanoate, 100.8 g (0.71 mol) of vinyl caproate and 50 g of lipase PS was stirred for 32 hours at room temperature. After lipase PS was removed by suction filtration, the filtrate was purified by distillation, and 133 g of R-methyl 2-hydroxydecanoate, b.p. 2 Torr 98°–111° C., $[\alpha]_D^{26} -2.58°$ (neat), 86%ee, and 172.8 g of S-methyl 2-caproyloxydecanoate, $[\alpha]_D^{26} -11.5°$ (neat), 64%ee, as the residue were obtained.

(2) A mixture of 131 g (0.56 mol) of R-methyl 2-hydroxydecanoate obtained in (1), 16 g (0.11 mol) of vinyl caproate and 30 g of lipase PS was stirred for 21 hours at room temperature. After lipase PS was removed by suction filtration, the filtrate was purified by distillation, and 75 g of R-methyl 2-hydroxydecanoate, b.p. 4 Torr 112° C., $[\alpha]_D^{28} -3.16°$ (neat), 100%ee, yield:63% from the racemic compound was obtained.

We claim:

1. A process for producing an optically active α-hydroxyester, said process comprising reacting an ester with a racemic compound of the formula:

$$\begin{array}{c} \text{OH} \\ | \\ \text{A—CHCOOR} \end{array} \quad (I)$$

wherein

R is alkyl of 1–5 carbon atoms,

A is a member selected from the group consisting of alkyl of 1–20 carbon atoms, perfluorophenyl, 2-phenylethyl or a group of the formula:

$$\left[ \begin{array}{c} R^1 \\ \\ R^2 \end{array} \bigcirc - \bigcirc \right]_n$$

wherein n is 0 or 1, $R^1$ and $R^2$ are halogen, hydroxyl, alkyl of 1–20 carbon atoms, alkoxy, amino or hydrogen, under substantially anhydrous conditions and in the presence of lipase PS from *Pseudomonas fluorescens* which is capable of transesterifying an ester with the racemic compound (I) and obtaining an S- or R-alcohol represented by the formula $$\begin{array}{c} \text{OH} \\ | \\ \text{A—C*HCOOR} \end{array} \quad (II)$$

wherein R and A are the same as described above and the corresponding R- or S- ester of the alcohol represented by the formula:

$$\begin{array}{c} \text{OCOR}^3 \\ | \\ \text{A—CH—COOR} \\ * \end{array} \quad (III)$$

wherein R and A are the same as described above and $R^3$ is alkyl of 1 to 11 carbon atoms.

2. A process according to claim 1 wherein the ester is vinyl ester.

* * * * *